United States Patent [19]

Adair

[11] Patent Number: 4,869,717
[45] Date of Patent: Sep. 26, 1989

[54] GAS INSUFFLATION NEEDLE WITH INSTRUMENT PORT

[76] Inventor: Edwin L. Adair, 2800 S. University Blvd., Denver, Colo. 80210

[21] Appl. No.: 185,532

[22] Filed: Apr. 25, 1988

[51] Int. Cl.⁴ .............................................. A61M 5/32
[52] U.S. Cl. ...................................... 604/51; 604/164; 604/274; 604/26
[58] Field of Search ..................... 604/23, 26, 51, 158, 604/164, 170, 264, 274

[56] References Cited

U.S. PATENT DOCUMENTS

| | | | |
|---|---|---|---|
| 1,527,291 | 2/1925 | Zorraquin | 604/158 |
| 2,630,803 | 3/1953 | Baran | 604/158 |
| 3,840,008 | 10/1974 | Noiles | 604/158 |
| 3,982,533 | 9/1976 | Wiest | 604/26 |
| 4,096,860 | 6/1978 | McLaughlin | 604/158 |
| 4,424,833 | 1/1984 | Spector et al. | 604/167 X |
| 4,535,773 | 8/1985 | Yoon | 604/51 |
| 4,769,018 | 9/1988 | Wilson | 604/158 X |
| 4,808,168 | 2/1989 | Warring | 604/158 |

FOREIGN PATENT DOCUMENTS 2308346 11/1976 France ................... 604/158

Primary Examiner—Dalton L. Truluck
Attorney, Agent, or Firm—Fields, Lewis, Pittenger & Rost

[57] ABSTRACT

The disposable trochar in the form of a gas insufflation needle having a removable rod and needle portion within an outer sheath is provided. The rod has a blunt end and is retractable during insertion so that the needle edge cuts through the abdominal wall. Once passing through the wall the rod extends so as to protect the bowel from the sharp needle. A gas port provided for introducing gas through the rod and out a side passageway near the blunt end. After the abdomen is extended, the rod and needle can be removed as unit from the sheath and thrown away and a suitable instrument introduced through an instrument port having a separable diaphragm. The gas can continue to be introduced around the instrument and into the abdomen while the instrument is in place. After the required medical procedures are completed, the instrument is removed. Then the sheath and associated parts are removed and thrown away.

5 Claims, 2 Drawing Sheets

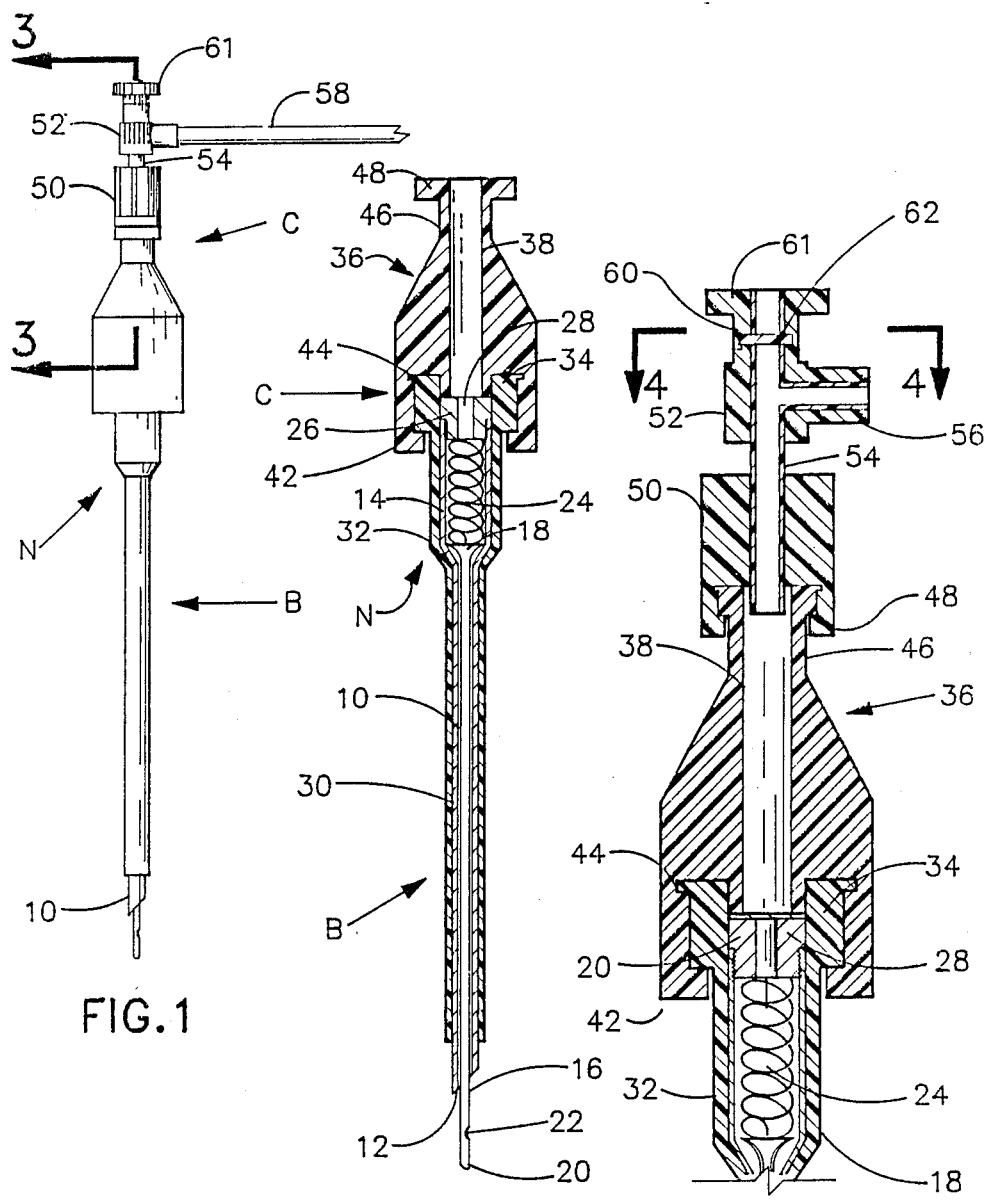

GAS INSUFFLATION NEEDLE WITH INSTRUMENT PORT

TECHNICAL FIELD

This invention relates to a disposable trochar, and more particularly to a trochar which includes a removable gas insufflation needle which can be used to inflate a body cavity with an inert gas, such as $CO_2$. After insufflation with the gas, the needle is removable and an instrument can be inserted in its place for carrying out a medical procedure.

BACKGROUND ART

The present invention is an improvement over the Veress Needle which was originally designed for insertion into the chest to collapse a lung in treatment of tuberculosis. Later, when laparoscopy was first introduced to allow surgeons to look into the peritoneal cavity, the needle found new usage in filling the abdominal cavity with carbon dioxide. The Veress Needle comprises an outer cannula which has a needle point for easy penetration of the skin and underlying structures in the abdominal wall. The outer cannula expands into a relatively long needle hub which is used to house a spring mechanism for retraction of an inner cannula. This inner cannula includes a hollow tube having an enclosed end which is rounded to help avoid injury of the intra-abdominal structures. There is a side hole spaced above the distal end of the inner cannula to allow flow of carbon dioxide gas. Thus, when the needle point is pushed through the skin and other structures of the abdominal wall, the inner cannula will retract against the bias of the spring mechanism so that the blunt point of the inner cannula is fully retracted within the inner cannula to allow easy penetration all the way through the abdominal wall. After the abdominal wall is penetrated, the inner, rounded tip, snaps forwardly into the space of the abdominal cavity and pushes underlying movable structures out of the way, such as large or small bowels, omentum or liver. The gas is then delivered to the abdominal cavity via a gas delivery system which is connected to the upper hub or valve section of the Veress Needle by a long plastic delivery tube. This gas creates a space or work area within the abdomen whereby good visualization is provided through a separate laparoscope. Any definitive surgical procedures, such as tubal ligations must be done through a separate opening.

Although the Veress Needle has been a very useful instrument for about fifty years, it has certain drawbacks. It is a complex design and therefore expensive to manufacture. Because of its construction and small parts, the parts can be lost during cleaning and it is virtually impossible to clean the side hole adjacent the blunt tip of the inner cannula, resulting in small pieces of tissue and tissue fluid being transferred from one patient to the next. Also, after repeated use, the point becomes dull. Furthermore, the needle can be dislodged if left in place during an entire operative procedure and must be reinserted. Also, because of the rigid construction, the sharp end may be driven into the abdomen and cause damage to intra-abdominal contents such as the bowel, liver or major blood vessels if accidentally bumped by the surgeon. Furthermore, the Veress Needle can only be used for gas delivery and is not usable for a port hole for introduction of a laparoscope, operating instruments, cautery devices, laser fiber or other devices. If these devices are used they must be introduced through an additional trochar which creates an additional incision in the patient.

Other instruments have been devised which comprise concentric cannulas for various procedures. None of them provide the advantages of the present invention as will be discussed below. Among these instruments are the following:

Baren U.S. Pat. No. 2,630,803 Baren shows a pneumothoracic needle with spring-loaded inner blunt needle and an outer sharp cannula. The inner blunt needle is hollow and is removable without extracting the cannula from the chest wall.

McLaughlin U.S. Pat. No. 4,096,860 discloses an encatheter incorporating a plastic insertion conduit placed into a blood vessel with a needle. The structure includes an elastomeric sealing flapper or one-way valve that allows insertion of a syringe needle.

Spector et al. U.S. Pat. No. 4,424,833 describes a molded self-sealing gasket assembly through which, for instance, a catheter may be inserted and removed.

Yoon U.S. Pat. No. 4,535,773 shows a safety puncturing instrument and method using a shielding mechanism that is biased to protrude from the distal end of the instrument to shield its sharp, penetrating point after the point has penetrated.

Noiles U.S. Pat. No. 3,840,008 discloses a hypodermic needle for safely injecting fluid into nerve and vessel crowded areas of a patient. The needle has a pointed hollow piercing member slidably mounted about a fluid delivery tube. The delivery tube has a blunt nose with at least one fluid opening near its blunt end, the other end being connected to a conventional syringe. The hollow piercing member is connected to the delivery tube by a finger-operated collapsible bar. The bar is provided with a centrally located groove to facilitate collapse at the moment the operator removes the force of his finger. The blunt nose delivery tube is then free to penetrate the tissue of the patient without endangering nerve or vessel.

DISCLOSURE OF THE INVENTION

In accordance with the present invention, a disposable trochar for use as gas insufflation needle is provided which includes an outer sheath having a tubular body, a distal and a proximate end, the proximate end having a flared hub of greater diameter than the body. An outer cannula is removably received within the sheath, the outer cannula having a sharp distal end extendable beyond the distal end of the sheath and an enlarged proximate end receivable within the flared hub of the proximate end of the sheath. An inner cannula is removably receivable within the outer cannula, the inner cannula having a flared proximate end which prohibits movement of the proximate end out of the enlarged proximate end of the outer cannula in the distal direction. A distal blunt end is extendable beyond the distal end of the outer cannula, the distal end having at least one side port therein for the discharge of gas. A removable cap is attachable to the proximate end of the outer cannula to limit movement of the inner cannula, the cap having an opening therein for transmitting gas to the inner cannula for discharge through the side port. The gas insufflation needle can be used for introduction of $CO_2$ gas and is ported for simultaneously receiving medical instruments for diagnostics and/or treatment through an abdominal wall.

Described another way, the trochar includes a rigid cannula having a cutting edge on the distal end for cutting through the abdominal wall. A sheath for slidably receiving and holding the cannula during insertion through the abdominal wall is provided for maintaining an opening therethrough after removal of the cannula from the sheath. A gas supplying tube is slidably received within the cannula and has a blunt end with at least one lateral opening adjacent thereto. The tube is selectively movable from an extended position wherein the blunt end extends beyond the cutting edge and a retracted position wherein the blunt end does not extend beyond the cutting edge. A resilient means is provided within the cannula urging the tube toward the extended position. The tube may have a flared proximate end to limit its movement in the extended position. The cannula has an enlarged proximate end for receiving the resilient means and the sheath has an enlarged proximate end for receiving the enlarged proximate end of the cannula. The cannula has a cap attached to the proximate end thereof and has an opening therethrough which is aligned with the tube. A hub closure attaches to the proximate end of the sheath with a concentric depending sleeve having a longitudinal passageway aligned with the cap opening, the sleeve serving as a stop to position the cannula within the sheath and being removable to remove the cannula and tube and reattach both for subsequent insertion of a medical instrument through the passageway, opening and sheath. The cannula and the tube are removable as a unit. A coil spring can serve as a resilient means and is in the enlarged proximate end of the cannula extending from the flared end of the tube to the cap.

With the insufflation needle of this invention, a novel method of inserting a medical instrument into a body cavity through an abdominal wall is possible. This method includes the steps of pressing the sharpened end of the cannula against the skin of the abdomen to cause the rod to be retracted. Next, the sharpened end of the cannula is thrust through the abdomen into the space between the peritoneum and the bowel to position the sheath through the opening formed by the cannula. Then the rod is extended beyond the sharpened end into the space between the peritoneum and the bowel. Next, gas is introduced through the rod to inflate the abdomen. Following this, the rod and the cannula are removed while the sheath remains in place and the instrument is introduced into the space through the sheath. Finally, gas can be reintroduced through the sheath while the instrument is in place to keep the abdomen inflated.

From the foregoing, the advantages of this invention are readily apparent. It is possible to form a very small incision or puncture opening through an abdominal wall with the insufflation needle of the trochar of this invention and use the same opening for inserting appropriate instrumentation for visualization of the internal body site or for conducting a surgical treatment or procedure. Furthermore, it is possible to keep the abdomen distended with gas during the viewing and/or surgical procedure through the same opening through which the instrumentation extends. Thus, discomfort and recovery of the patient is minimized. Also, the trochar is of such simple construction that it is thrown away after one use. Thus, the problems of cleaning and contamination of one patient to another are eliminated.

Additional advantages will become apparent from the description which follows, taken in conjunction with the accompanying drawings.

BRIEF DESCRIPTION OF THE DRAWINGS

FIG. 1 is a side elevation of a disposable trochar in the form of an insufflation needle constructed in accordance with this invention;

FIG. 2 is a longitudinal section of the insufflation needle of FIG. 1, on an enlarged scale;

FIG. 3 is a greatly enlarged vertical section, taken along 3—3 of FIG. 1 showing the connection of the insufflation needle to a source of $CO_2$ gas;

FIG. 4 is an enlarged cross-section, taken along line 4—4 of FIG. 3, showing the diaphragm for providing a gas seal in the instrument port;

BEST MODE FOR CARRYING OUT THE INVENTION

Figure 5:
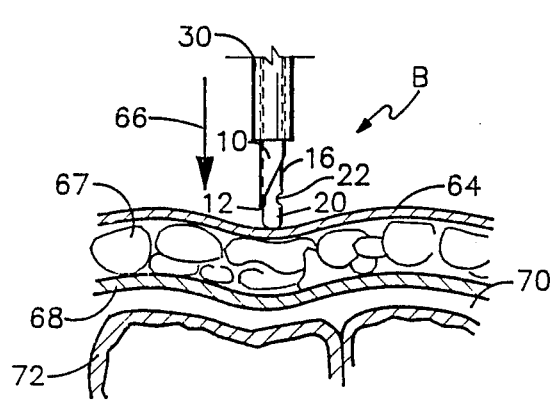
FIG. 5 is diagrammatical view of a portion of the abdomen showing the positioning of the insufflation needle prior to insertion.

In accordance with this invention a disposable trochar in the form of a gas insufflation needle N is provided which has an elongated body section B having a distal end for insertion through an abdomen wall into a body cavity and a proximate end having a connector portion C. The trochar has a rigid cannula or needle 10 having a sharp distal edge or end 12 for easy penetration of the skin and underlying structures in the abdominal wall, as will be explained below, and an enlarged proximate end 14. This outer cannula or needle is conveniently made of surgical steel and is approximately 0.082 inches in outside diameter and 6 inches long. The length of the needle can be either longer or shorter, depending upon particular requirements. An inner cannula in the form of a tubular rod 16 is slidably received within needle 10. Its proximate end has a flared portion 18 which limits its movement in the distal direction. The distal end 20 is blunt, being closed and rounded and has a side opening 22 for the passage of a discharging gas, such as $CO_2$. A spring 24, in the form of a coil spring, is received in the enlarged end 14 of needle 10 and is held in place by threaded cap 26 having a central opening 28 therethrough. The inner cannula or rod 16 is also made of surgical steel.

The above described parts are received in a sheath made of plastic, such as Teflon, having an elongated body portion surrounding needle 10 but slightly shorter in length than the outer cannula, i.e., about 5½ inches long. Its thickness is on the order of 0.015 inches. The proximate end of sheath 30 is flared to form a hub 32 for receiving enlarged end 14 of the needle. The hub 32 terminates in an upper rib or flange 34 for receiving a hub closure 36. This hub may be made of polycarbonate and may have a thickness on the order of 0.030 inches. It is about ⅞ inches in length. The hub closure has a central passageway 38 in communication with central opening 28. At the lower or distal end of passageway 38 is a depending sleeve 40 having a face 41 which bears against cap 26 to hold needle 10 in fixed position within sheath 30. The hub closure 36 also includes a depending peripheral flange 42 having locking means, such as a Luer lock 44 for releasable locking engagement with a mating portion on flange 34. The upper end of hub closure 36 terminates in a neck 46 having a Luer lock 48 at the end thereof.

The connecting portion C includes a connector fixture 50 and a tee 52 spaced therefrom. A conduit 54 extends from connector 50 and tee 52, joining the two together. Gas is supplied as through gas port 56 of tee 54. The other port 60 is an instrument port for the passage of an instrument through sheath 30 after the removal of needle 10. It has a Luer lock fitting 61 for releasably locking an instrument in place, such as an endoscope as will be more fully explained below. Also, port 60 is provided with a diaphragm 62 comprising overlapping membranes, as best seen in FIG. 4. As shown, diaphragm 62 has two overlapping membranes, each of which extends more than one-half the distance across the instrument port. Thus, this diaphragm 62 provides a seal against the escape of gas when gas is introduced through gas port 56 via conduit 58 and when an instrument is inserted through port 60 and diaphragm 62, it will tend to conform with the outer periphery of the instrument so as to minimize the leakage of gas therearound.

Figure 6:
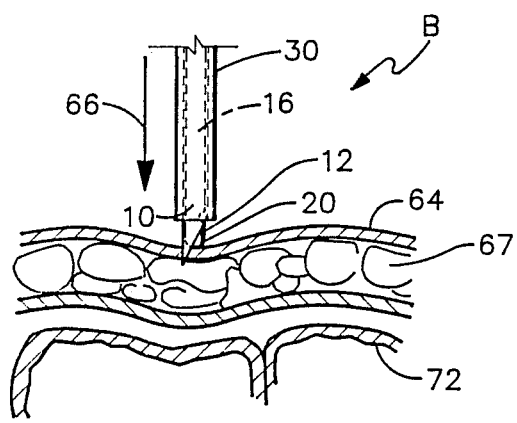
FIG. 6 is a view, similar to FIG. 5 but showing the beginning of the penetration of the needle through the abdominal wall.
Figure 7:
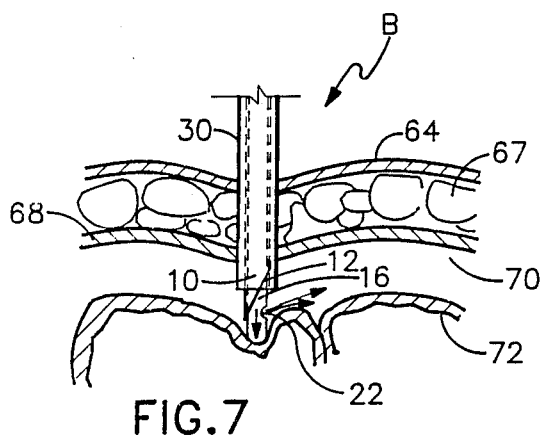
FIG. 7 shows the insufflation needle in place within the abdominal cavity.

The insufflation needle of this invention is inserted into the abdomen as illustrated in FIGS. 5, 6 and 7. To insert the insufflation needle, the blunt end 20 of rod 16 is pressed against the surface of skin 64 and the needle is thrust downwardly against the skin in the direction indicated by arrow 66. This motion causes the rod 16 to be retracted against the force of spring 24 into needle 10. This exposes the sharp edge 12 of needle 10 which pierces the skin 64 and fat 67 as shown in FIG. 5. The needle then passes through the peritoneum 68 into the air space 70 formed between the peritoneum and bowel 72. When the needle enters the air space 70, there is no longer any pressure against the blunt end 20 of rod 16 so that it again is extended and protects the bowel from the sharp edge 12 of needle 10. A gas, such as carbon dioxide, can be introduced through conduit 56 so as to pass through conduit 52 and passageway 38. The gas then passes through central opening 26 in cap 26 and down through rod 16 and out through side opening 22 into the air space. The gas may be introduced at sufficient pressure to distend the abdominal cavity to a considerable extent.

Figure 8:
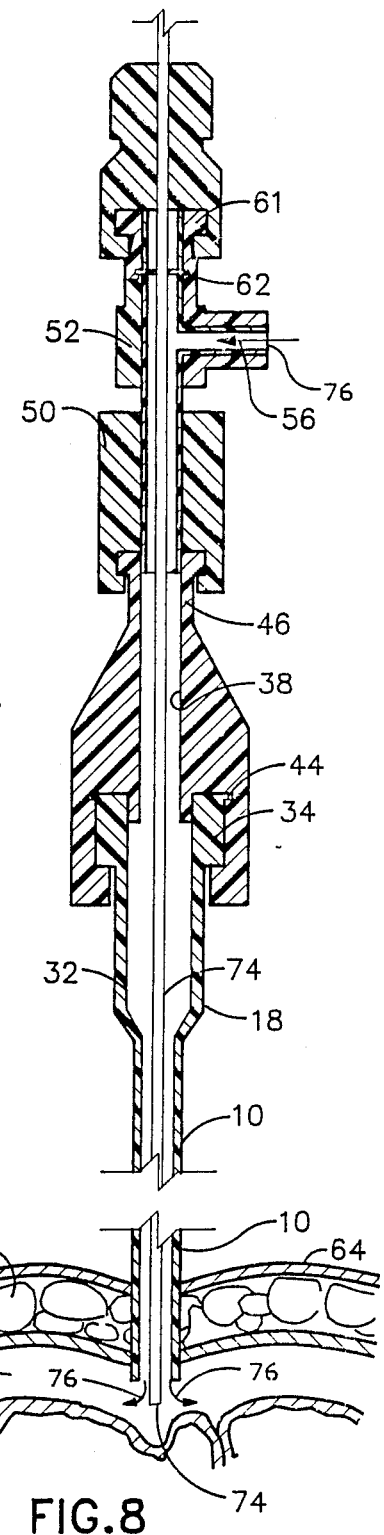
FIG. 8 shows the insufflation needle in place with the needle replaced by an endoscope.

Once this has been accomplished, hub closure 36 is removed from flange 34 of hub 32 whereupon needle 10 and rod 16 can be removed as a unit and thrown away while sheath 30 remains in place. The hub closure is then reattached so that gas can continue to be introduced to the abdomen, as needed. Conveniently, an instrument, such as laser endoscope 74, seen in FIG. 8 can be introduced through instrument port 60 and pass through the overlapping edges of diaphragm 62 down through the passageway and space previously occupied by the needle and rod. It includes a spin lock 75 which releasably engages Luer lock 61 to hold the endoscope. The gas can continue to be introduced, as needed and will flow through the space formed between instrument 74 and sheath 30, as shown by arrows 76. Also, one instrument can be removed and another one inserted through the sheath 30, as required. When all procedures are completed, the instrument can be removed. Then the sheath and associated parts can be removed and thrown away.

From the foregoing, the advantages of this invention are readily apparent. A disposable insufflation needle has been provided which can be used to introduce gas into an abdominal cavity to extend the same while at the same time introducing a suitable instrument, all being accomplished through a single incision made by the trochar. Conveniently, the insufflation needle includes a spring loaded rod within a needle which is removable from an outer sheath after the device is inserted in the abdomen. During insertion, the rod is retracted and the needle inserted through the skin whereupon the rod extends under the influence of a spring bias so as to protect the bowel or other organs from the sharp edge of the needle. Then, the rod and needle can be removed together to provide a passageway for other instrumentation for running appropriate procedures and/or operations on the patient. At the same time gas can continue to be introduced through the sheath around the instrument.

This invention has been described in detail with reference to particular embodiments thereof, but it will be understood that various other modifications can be effected within the spirit and scope of this invention.

I claim:

1. A disposable trochar for use as a gas insufflation needle said trochar comprising:
    an outer sheath having a tubular body, a distal end and a proximate end, said proximate end having a flared elongated hub of greater internal diameter than said body;
    an outer cannula removably received within said sheath, said outer cannula having a sharp distal end extendable beyond said distal end of said sheath and an enlarged elongated proximate end which has an outer diameter and shape configured to be receivable within said flared hub of said elongated proximate end of said sheath;
    an inner cannula removably received within said outer cannula, said inner cannula having a short flared proximate end positionable within said elongated proximate end of said outer cannula, which prohibits movement of said proximate end out of said enlarged proximate end of said outer cannula in the distal direction, and a distal blunt end extendable beyond said distal end of said outer cannula, said distal end having at least one side port therein for the discharge of gas;
    a removable cap attached to said proximate end of said outer cannula to limit inward movement of said inner cannula within said outer cannula, said cap having an opening therein for transmitting gas to said inner cannula for discharge through said side port;
    a generally hollow hub closure releasably secured to said hub for holding said outer cannula within said sheath and having an elongated body with a central passageway for the passage of instruments or gas;
    a releasable locking means on the exterior surface of the proximate end of said tubular body;
    a cup-shaped flange on the distal end of said elongated body for enclosing said proximate end of said sheath;
    releasable locking means on the interior surface of said flange for releasably engaging said proximate end of said hub; and
    a concentric member within said flange for holding said outer cannula in fixed position within said sheath.

2. A disposable trochar in the form of a gas insufflation needle for insertion through an abdominal wall for the simultaneous introduction of $CO_2$ gas and medical instruments for diagnostics and/or treatment, said trochar comprising:

a rigid cannula having a cutting edge on the distal end thereof for cutting through the abdominal wall and an enlarged elongated proximate end;

a sheath for slidably receiving and holding said cannula during insertion through the abdominal wall and maintaining an opening therethrough after removal of said cannula from said sheath and having an elongated enlarged proximate end whose inner diameter and shape is configured to slidably receive said proximate end of said cannula;

a gas supplying tube slidably received within said cannula and having a blunt distal end with at least one lateral opening adjacent thereto and a flared proximate end slidable within said elongated enlarged proximate end of said cannula, said tube being selectively movable from an extended position wherein said blunt end extends beyond said cutting edge, the extension being limited by said flared end, and a retracted position wherein said blunt end does not extend beyond said cutting edge;

a cap attached to the proximate end of said elongated enlarged proximate end of said cannula and has an opening therethrough which is aligned with said tube;

resilient means within said elongated enlarged proximate end of said cannula extending between said cap and said flared end of said tube urging said tube toward said extended position and a hub closure attached to said proximate end of said sheath with a concentric depending sleeve having a longitudinal passageway aligned with said cap opening, said sleeve serving as a stop to position said cannula within said sheath and being removable to remove said cannula and tube and reattachable for subsequent insertion of a medical instrument through said passageway, opening and sheath.

3. Apparatus, as claimed in claim 2, wherein:
said cannula and said tube are removable as a unit.

4. A method of insertion a medical instrument into a body cavity through an abdominal wall utilizing a insufflation needle which has a cannula with a sharpened distal end, a sheath surrounding the cannula and a retractable tube for supplying a gas for discharge through an opening adjacent the blunt distal end of the tube which is slidable within the cannula from the retracted position to an extended position beyond the sharpened end, said method comprising the steps of:

pressing the sharpened end of the cannula against the skin of the abdomen to cause the rod to be retracted;

thrusting the sharpened end of the cannula through the abdomen into the space between the peritoneum and the bowel to position the sheath through the opening formed by the cannula;

extending the rod beyond the sharpened end into the space between the peritoneum and the bowel;

introducing a gas through the rod to inflate the abdomen;

removing the rod and cannula while the sheath remains in place;

introducing an instrument into the space through the sheath.

5. The method of claim 4, including the further step of:

reintroducing gas through the sheath while an instrument is in place.

* * * * *

UNITED STATES PATENT AND TRADEMARK OFFICE
CERTIFICATE OF CORRECTION

PATENT NO.  : 4,869,717

DATED       : September 26, 1989

INVENTOR(S) : Edwin L. Adair

It is certified that error appears in the above-identified patent and that said Letters Patent is hereby corrected as shown below:

Column 8, line 9, after "insertion" insert --of--;
lines 19, 25, 27 and 29, respectively, delete "rod" and insert --tube--.

Signed and Sealed this

Seventh Day of January, 1992

Attest:

HARRY F. MANBECK, JR.

*Attesting Officer*   *Commissioner of Patents and Trademarks*